United States Patent [19]

Bartmann

[11] Patent Number: 4,980,508
[45] Date of Patent: Dec. 25, 1990

[54] PROCESS FOR THE PREPARATION OF 1,2-DISULFONE COMPOUNDS

[75] Inventor: Ekkehard Bartmann, Erzhausen, Fed. Rep. of Germany

[73] Assignee: Merck Patent Gesellschaft Mit Beschrankter Haftung, Darmstadt, Fed. Rep. of Germany

[21] Appl. No.: 308,483

[22] Filed: Feb. 10, 1989

[30] Foreign Application Priority Data

Feb. 12, 1988 [DE] Fed. Rep. of Germany ....... 3804316

[51] Int. Cl.$^5$ .................. C07C 315/00; C07C 317/00
[52] U.S. Cl. ....................................... 568/22; 568/28; 568/34
[58] Field of Search ............................. 568/28, 34, 22

[56] References Cited

PUBLICATIONS

Chemical Abstracts, vol. 88, p. 502, yr. 1978, 136243f.
Kwart et al., Journal of Organic Chemistry, vol. 33 #4, 1968, pp. 1537–1542.
Walkaff et al., Chemical Abstracts, vol. 81, p. 435, 1974, 77619p.

Primary Examiner—Mukund J. Shah
Assistant Examiner—Deborah D. Carr
Attorney, Agent, or Firm—Millen, White & Zelano

[57] ABSTRACT

The invention relates to a process for the preparation of 1,2-disulfone compounds by oxidation of corresponding 1,2-disulfonylhydrazine compounds with the aid of concentrated nitric acid as the oxidizing agent.

12 Claims, No Drawings

PROCESS FOR THE PREPARATION OF 1,2-DISULFONE COMPOUNDS

BACKGROUND OF THE INVENTION

The invention relates to a process for the preparation of 1,2-disulfone compounds.

1,2-Disulfone compounds have diverse potential uses. It is known, for example, from Bull. Chem. Soc. Jap. 45, 2906 (1972) (CA 78:15196c) that diaryldisulfones are photoreactive and dissociate into radicals under the action of radiation. According to JP No. 58-83844 (CA 101: 63684a) such compounds are used as agents which produce free radicals in photosensitive compositions for photolithographic purposes. According to Makromol. Chem., Rapid Commun. 4, 539 (1983) (CA 99: 140979v) and JP No. 59-197422 (CA 102: 186029u), diaryldisulfones can be used as agents which crosslink by radiation for epoxy-functionalized acrylate polymers. 1,2-Disulfones are moreover useful reagents and synthesis intermediates, for example in the synthesis of pharmaceutically active compounds.

A preparation process for 1,2-disulfones having a wide range of substituents, with, in principle, any desired radical, and which is easy to carry out has not heretofore been known.

According to JP No. 58-83844, diaryldisulfones are accessible by reaction of alkali metal arylsulfinates with arylsulfonyl chlorides. This method is expensive, especially when used to obtain unsymmetrically substituted disulfones. The product yields which can be achieved are moreover unsatisfactory.

A synthesis route which is simple in principle is described in Z. Naturforsch. 21b, 813 (1966). In this article, symmetrical phenyl, p-tolyl and naphthyl disulfones were prepared by oxidation of the corresponding disulfonyl hydrazines, and yields of between about 30 and 50% were achievable. Only mercury oxide and N-bromosuccinimide were used as oxidizing agents. The choice of these oxidizing agents, which are unusual because they are expensive, and, in the case of mercury oxide also problematical, and all in all are to be described as "exotic", suggests that customary oxidizing agents were not successful in this reaction.

SUMMARY OF THE INVENTION

In fact, it has been found that practically all the customary oxidizing agents are unsatisfactory or completely unsuitable for this reaction. It was found completely surprisingly, however, that concentrated nitric acid is an outstandingly suitable oxidizing agent for this reaction. It was particularly unexpected here that in addition to symmetric and unsymmetric diaryldisulfones, arylalkyldisulfones, dialkyldisulfones and variously substituted aryldisulfones and also heteroaromatic disulfones can also be prepared without problems with the aid of concentrated nitric acid.

The invention thus relates to a process for the preparation of 1,2-disulfone compounds by oxidation of corresponding 1,2-disulfonylhydrazine compounds, the oxidation being carried out with concentrated nitric acid as the oxidizing agent.

Diverse 1,2-disulfones with essentially any desired organic radicals can be prepared by the process according to the invention. These are, in particular, 1,2-disulfone compounds of the formula I $$R^1-SO_2-SO_2-R^2 \qquad (I)$$

wherein $R^1$ and $R^2$ can be identical or different and are alkyl, cycloalkyl, aryl, aralkyl or heteroaryl, each having up to 12 C atoms and optionally substituted by one or more substituents from the group comprising halogen, cyano, nitro, carboxyl, alkyl, alkoxy, alkylthio, bisalkylamino, alkanoyl, alkanoyloxy, alkanoylamido, alkoxycarbonyl, alkylaminocarbonyl, alkylsulfoxy, alkylsulfonyl, aryloxy, arylthio, arylsulfoxy and arylsulfonyl having in each case up to 6 C atoms.

The 1,2-disulfonylhydrazine compounds to be used as starting substances are accessible in a simple manner by known methods, e.g., by the reaction of hydrazine with corresponding sulfonyl chlorides. It is also possible to obtain the unsymmetric 1,2-disulfonylhydrazine compounds by a stepwise reaction.

The overall course of the reaction can be represented by the following equation:

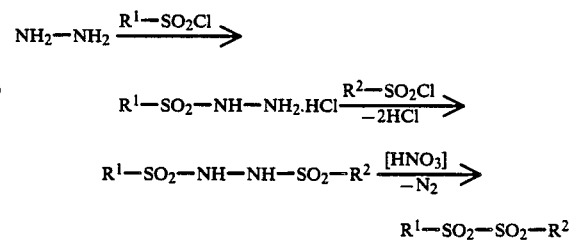

The oxidation reaction to give the 1,2-disulfone is carried out according to the invention by adding concentrated nitric acid having a density of about 1.4 and a purity which is customary for synthesis purposes to the corresponding 1,2-disulfonylhydrazine compound, preferably while stirring and cooling. Since the reaction components can be reacted with one another directly, the presence of a solvent can be dispensed with. The temperature of the reaction mixture during the addition and reaction is kept in the range from −5° to +5° C., preferably at about 0° C. These conditions are obtained, e.g., by cooling the reaction vessel with ice. The reaction usually starts after a few minutes, with evolution of nitrogen. The product which has precipitated as a solid precipitate or is precipitated by addition of water after the end of the reaction may be purified by recrystallization, if required.

In many cases, it is also possible to carry out the entire reaction sequence, e.g., the reaction of hydrazine to give 1,2-disulfonylhydrazine and the subsequent oxidation to the 1,2-disulfone, in a "one-pot reaction" without isolation of the disulfonylhydrazine or, if appropriate, the monosulfonylhydrazine intermediate stage. This makes the process according to the invention particularly simple and economic.

A large number of widely differently substituted 1,2-disulfone compounds can be obtained in a form which is easy to isolate and in an outstanding to at least satisfactory yield using the oxidizing agent according to the invention. In contrast, with a large number of other customary oxidizing agents, such as, for example, hydrogen peroxide, potassium permanganate, potassium chlorate, chlorine or bromine, to single out only a few typical representatives, either no reaction was to be recorded or the reaction led to the disulfone to only a minor degree, if at all. Only with sodium hypochlorite was it possible in a very few cases, in particular in the case of disulfones of the formula I in which $R^1$ and $R^2$ are phenyl or p-tolyl, to obtain these in a moderate yield. In all other cases, this reagent also failed.

The method of nitric acid oxidation is also particularly advantageous for the preparation of diaryldisulfones which carry sensitive substituents, e.g., substituents which tend to undergo secondary reactions, on the aryl radicals. Because of its comparatively mild conditions, the method is even compatible for many substituents which are rapidly oxidized or converted in other ways by other oxidizing agents. Thus, for example, sodium hypochlorite causes partial chlorination of i-propyl, acetamido and dimethylmaleimido radicals on the aromatic, whereas nitric acid leads to the corresponding 1,2-disulfone without problems in these cases.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents, and publications, if any, cited above and below, and of corresponding application German No. P 38 04 316.5, filed Feb. 12, 1988, are hereby incorporated by reference.

EXAMPLES

A. General instructions for the preparation of 1,2-disulfones of the formula $R^1-SO_2-SO_2-R^2$ (I)

Concentrated nitric acid (density 1.4) is added dropwise to the corresponding 1,2-disulfonylhydrazine compound, while stirring and cooling with ice. After a few minutes, the reaction starts with evolution of nitrogen. When the reaction has subsided, the mixture is stirred at 0° C. for about 1 hour and the precipitate which has separated out is removed and recrystallized for purification.

B. Compounds prepared

| No. | $R^1$ | $R^2$ | Recrystallized from | Melting point (°C.) |
|---|---|---|---|---|
| 1 | Phenyl | Phenyl | Ethanol | 192 |
| 2 | Phenyl | 4-Methylphenyl | Methanol | 177 |
| 3 | Phenyl | 4-Methoxyphenyl | Acetone | 153 |
| 4 | Phenyl | 2-Naphthyl | Methyl t-butyl ether | 182 |
| 5 | Phenyl | Benzyl | Methyl t-butyl ether/acetone | 186 |
| 6* | Phenyl | 2-Nitro-3,5-dimethoxyphenyl | Acetone | 186 |
| 7 | Phenyl | 2,4,6-Trimethylphenyl | Toluene | 154 |
| 8 | Phenyl | 4-i-Propylphenyl | Glacial acetic acid | 92 |
| 9 | Phenyl | 4-Chlorophenyl | Toluene | 181 |
| 10 | Phenyl | 4-Bromophenyl | Acetone | 198 |
| 11 | 4-Methylphenyl | 4-Methylphenyl | Acetone/ether | 222 |
| 12 | 4-Methylphenyl | 4-Chlorophenyl | Toluene | 206 |
| 13 | 4-Methylphenyl | Benzyl | Methanol | 126 |
| 14 | 4-Methylphenyl | 2-Naphthyl | Methyl t-butyl ether/methylene chloride | 186 |
| 15 | 4-Methylphenyl | 4-Methoxyphenyl | Acetone | 173 |
| 16* | 4-Methylphenyl | 2-Nitro-3,5-dimethoxyphenyl | Acetone | 182 |
| 17 | 4-Methylphenyl | Methyl | Methyl t-butyl ether | 109 |
| 18 | 4-Methylphenyl | 1-Naphthyl | Acetone | 201 |
| 19 | 1-Naphthyl | 1-Naphthyl | Acetone/dimethylformamide | 183 (decomposition) |
| 20 | 2-Naphthyl | 2-Naphthyl | Tetrahydrofuran | 226 (decomposition) |
| 21 | 4-Methoxyphenyl | 4-Methoxyphenyl | Acetone | 194 (decomposition) |
| 22 | 4-Nitrophenyl | 4-Nitrophenyl | Tetrahydrofuran | 224 (decomposition) |
| 23 | 2-Methylphenyl | 2-Methylphenyl | Toluene | 160 |
| 24 | Benzyl | Benzyl | Glacial acetic acid | 183 (decomposition) |
| 25 | Benzyl | n-Propyl | Methylene chloride/n-pentane | 100 |
| 26 | n-Propyl | n-Propyl | (Water)** | 53 |
| 27 | n-Propyl | 4-Nitrophenyl | Methyl t-butyl ether | 111 |

-continued

| No. | R¹ | R² | Recrystallized from | Melting point (°C.) |
|---|---|---|---|---|
| 28 | n-Propyl | 4-Methoxyphenyl | Petroleum ether | 83 |
| 29 | Phenyl | n-Propyl | Methyl t-butyl ether | 138 |
| 30 | Phenyl | 4-t-Butylphenyl | (Water)** | 128 |
| 31 | 4-Methylphenyl | n-Propyl | (Water)** | 86 |
| 32 | 4-i-Propylphenyl | Methyl | — | (oil) |
| 33 | 4-t-Butylphenyl | n-Propyl | Ether/petroleum ether | 110 |
| 34 | 1-Naphthyl | Methyl | Toluene | 157 |
| 35 | 1-Naphthyl | n-Propyl | (Water)** | 116 |
| 36 | 2-Naphthyl | Methyl | (Water)** | 146 |
| 37 | 2-Naphthyl | n-Propyl | Ether/petroleum ether | 67 |
| 38 | 4-Acetylamidophenyl | n-Propyl | Glacial acetic acid | 189 |
| 39 | 4-Acetylamidophenyl | Phenyl | Glacial acetic acid | 208 |
| 40 | 4-Acetylamidophenyl | 4-Methylphenyl | Glacial acetic acid | 201 |
| 41 | 4-Acetylamidophenyl | 4-Methoxyphenyl | Glacial acetic acid | 204 |
| 42 | 4-Acetylamido- | 4-Nitrophenyl | Glacial acetic acid | 198 (decomposition) |
| 43 | 4-Phthalimidophenyl | n-Propyl | Glacial acetic acid | 196 |
| 44 | 4-Phthalimidophenyl | Phenyl | Methylene chloride/cyclohexane | 210 |
| 45 | 4-Phthalimidophenyl | 4-Methylphenyl | Glacial acetic acid | 214 |
| 46 | 4-Phthalimidophenyl | 4-Methoxyphenyl | Glacial acetic acid | 162 |
| 47 | 4-(1,2-dimethylmaleimido)phenyl | n-Propyl | Methyl t-butyl ether | 143 |
| 48 | 4-(1,2-dimethylmaleimido)phenyl | Phenyl | Methylene chloride | 222 |
| 49 | 4-(1,2-dimethylmaleimido)phenyl | 4-Methylphenyl | Methylene chloride/petroleum ether | 235 |
| 50 | 4-(1,2-dimethylmaleimido)phenyl | 4-Methoxyphenyl | Glacial acetic acid | 162 |
| 51 | 4-Nitrophenyl | n-Propyl | Ether | 104 |

*The NO₂ group was introduced here during the nitric acid oxidation
**Already crystallizes out in a sufficient purity on addition of water

C. Comparative oxidation experiments

The suitability of other oxidizing agents for some of the 1,2-disulfone compounds prepared in B. was tested in comparison with the method of oxidation with concentrated nitric acid. The other oxidizing agents were used under the reaction conditions customary for them.

In the following Table 1, the symbols are as follows:
++ : disulfone can be isolated in a good yield
+ : disulfone can be isolated in a moderate yield
o: disulfone detectable in a small amount but cannot be isolated
—: disulfone not detectable; other reaction products
=: no reaction

TABLE 1

| Compound No. | Comparative oxidation experiments | | | | | | | | | | | | | |
|---|---|---|---|---|---|---|---|---|---|---|---|---|---|---|
| | 1 | 2 | 8 | 11 | 13 | 24 | 25 | 29 | 31 | 32 | 33 | 36 | 37 | 41 | 44 |
| HNO₃ | ++ | ++ | ++ | ++ | + | + | + | ++ | ++ | ++ | ++ | ++ | ++ | ++ | ++ |
| NaOCl/H₂O | + | + | o | + | — | — | | o | o | — | o | — | — | — | + |
| H₂O₂/Na₂WO₄ | = | | | | | | | | | | | | | | |
| K₂S₂O₈/H₂SO₄ | | | | | | | = | | | | | | | | |
| N-Bromosuccinimide/CH₂Cl₂ | | | | | | | — | | — | | | | | | |
| K₃Fe(CN)₆ | | = | | | | | | | | | | | | | |
| Benzoyl peroxide/chlorobenzene | | | | | | | = | | | | | | | | |
| Bleaching powder | | | | | | | = | | | | | | | | |
| Ce^{IV}H₃O⁺ | | | | | | | — | | | | | | | | |
| KClO₃/H₃O⁺ | | | | | | | = | | | | | | | | |
| KMnO₄/Acetone | | | | | | | = | | | | | | | | |
| KMnO₄/CH₃CO₂H | | | | | | + | — | | | o | | | | | |
| m-Chloroperbenzoic acid/CH₂Cl₂ | + | | | | | | | — | — | | o | | | | |
| Cl₂H₂SO₄ | | | | | | — | | | | | | | | | |
| Cl₂/CCl₄ | | | | | | — | | | — | | | | | | |
| Br₂/C₂H₅OH | | o | | | | | | | | | | | | | |

TABLE 1-continued

| Compound No. | Comparative oxidation experiments | | | | | | | | | | | | | |
|---|---|---|---|---|---|---|---|---|---|---|---|---|---|---|
| | 1 | 2 | 8 | 11 | 13 | 24 | 25 | 29 | 31 | 32 | 33 | 36 | 37 | 41 | 44 |
| Br$_2$/H$_2$SO$_4$ | | | | | — | — | | | | | | | | |
| Br$_2$/CH$_3$CO$_2$H | | — | | o | — | — | — | | | | | | | |
| H$_2$O$_2$/HCl/H$_2$O | | | | = | | | | | | | | | | |
| H$_2$O$_2$/HCO$_2$H | = | | | | | | | | | | | | | |
| H$_2$O$_2$/CH$_3$CO$_2$H | | | | = | | | | | | | | | | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of 1,2-disulfone compounds of the formula:

$$R^1-SO_2-SO_2-R^2$$

wherein $R^1$ and $R^2$ are identical or different and are substituted or unsubstituted alkyl, cycloalkyl, aryl, aralkyl or heteroalkyl having up to 12 carbon atoms, comprising oxidizing a 1,2-disulfonyl hydrazine compound of the formula:

$$R^1-SO_2-NH-NH-SO_2-R^2$$

wherein $R^1$ and $R^2$ are as defined above in the presence of an oxidation agent which comprises concentrated nitric acid.

2. A process according to claim 1, wherein $R^1$ and/or $R^2$ is substituted with halogen, cyano, nitro, carbonyl, alkyl, alkoxy, alkylthio, bisalkylamino, alkanoyl, alkanoyloxy, alkanoylamido, alkoxycarbonyl, alkyl aminocarbonyl, alkyl sulfoxy, alkyl sulfonyl, aryloxy, arylthio, arylsulfoxy, and arylsulfonyl, wherein each substituent has up to 6 carbon atoms.

3. A process according to claim 1, wherein said process is conducted at a temperature of $-5°$ to $5°$ C.

4. A process according to claim 1, wherein the 1,2-disulfonylhydrazine compound is produced by reacting hydrazine with the corresponding sulfonyl chloride.

5. A process according to claim 4, wherein the 1,2-disulfonyl hydrazine is oxidized to produce the 1,2-disulfone without separation of the reaction mixture from the 1,2-disulfonyl hydrazine reaction.

6. A process according to claim 1, wherein said process is carried out in the absence of a solvent.

7. In a process for the production of 1,2-disulfone compounds by oxidation of the corresponding 1,2-disulfonylhydrazine compounds in the presence of an oxidizing agent, the improvement comprising using as an oxidizing agent concentrated nitric acid.

8. A process according to claim 7, wherein said process is carried out at a temperature of $-5°$ to $5°$ C.

9. A process according to claim 7, wherein said process is carried out in the absence of a solvent.

10. A process according to claim 7, wherein said concentrated nitric oxide has a density of about 1.4.

11. A process according to claim 1, wherein $R^1$ and/or $R^2$ is aryl.

12. A process according to claim 11, wherein $R^1$ and/or $R^2$ are substituted by alkyl or alkoxy.

* * * * *